(12) United States Patent
Wang et al.

(10) Patent No.: US 7,801,349 B2
(45) Date of Patent: Sep. 21, 2010

(54) AUTOMATIC GENERATION OF AN ENVELOPE OF CONSTRAINT POINTS FOR INVERSE PLANNING

(75) Inventors: Hongwu Wang, Milpitas, CA (US); Jay B. West, Mountain View, CA (US); John R. Dooley, Castro Valley, CA (US)

(73) Assignee: Accuray Incorporated, Sunnyvale, CA (US)

( * ) Notice: Subject to any disclaimer, the term of this patent is extended or adjusted under 35 U.S.C. 154(b) by 1208 days.

(21) Appl. No.: 11/220,838

(22) Filed: Sep. 6, 2005

(65) Prior Publication Data

US 2007/0053490 A1 Mar. 8, 2007

Related U.S. Application Data

(60) Provisional application No. 60/692,606, filed on Jun. 20, 2005.

(51) Int. Cl.
*G06K 9/00* (2006.01)
*A61N 5/10* (2006.01)

(52) U.S. Cl. .................................. 382/131; 378/65

(58) Field of Classification Search ........... 128/920, 128/922, 923; 250/582; 345/204, 419, 424; 345/427; 356/12, 39; 377/10; 378/4, 8, 378/37, 64–65, 98.12, 98.8; 600/407–408, 600/411, 425–426, 454, 604; 606/130; 703/5; 382/128–134, 154, 219, 237, 274, 278, 100
See application file for complete search history.

(56) References Cited

U.S. PATENT DOCUMENTS

| | | | |
|---|---|---|---|
| 5,341,292 A | | 8/1994 | Zamenhof |
| 6,238,342 B1 * | | 5/2001 | Feleppa et al. ............ 600/437 |
| 6,556,199 B1 | | 4/2003 | Fang et al. |
| 6,757,423 B1 * | | 6/2004 | Amini ..................... 382/154 |
| 7,158,661 B2 * | | 1/2007 | Inoue ..................... 382/128 |
| 7,362,848 B2 * | | 4/2008 | Saracen et al. ............. 378/65 |
| 2002/0102023 A1 | | 8/2002 | Yamauchi |
| 2003/0053669 A1 * | | 3/2003 | Suri et al. .................. 382/130 |
| 2003/0065260 A1 | | 4/2003 | Cheng et al. |
| 2003/0072411 A1 | | 4/2003 | Welsh |
| 2003/0099397 A1 | | 5/2003 | Matsugu et al. |
| 2005/0201516 A1 | | 9/2005 | Ruchala et al. |
| 2005/0262467 A1 | | 11/2005 | Croffie |
| 2006/0072802 A1 | | 4/2006 | Higgs et al. |
| 2006/0274885 A1 | | 12/2006 | Wang et al. |
| 2006/0274925 A1 | | 12/2006 | West et al. |
| 2006/0293583 A1 * | | 12/2006 | Saracen et al. ............. 600/407 |
| 2007/0127623 A1 | | 6/2007 | Goldman et al. |

OTHER PUBLICATIONS

IEEE Transaction on Medical Imaging, vol. 17, No. 1, Feb. 1998 Automatic Detection of the Boundary of the Calcaneus from Ultrasound Parametric Images Using an Active Contour Model; Clinical Assessment; Francoise Lefebvre, Genevieve Berger, and Pascal Laugier IEEE 0278-0062/98 1998.*
IEEE Transaction on Medical Imaging, vol. 16, No. 6, Dec. 1997 Method for Segmenting Chest CT Image Data Using an Anatomical Model: Preliminary Results; Matthew S. Brown, Michael F. McNitt-Gray, Nicholas J. Mankovich, Jonathan G. Goldin, John Hiller, Laurence S. Wilson, and Denise R. Aberle IEEE 0278-0062/97 1997.*
U.S. Appl. No. 11/242,366, Final Office Action dated May 28, 2010, 14 pages.

(Continued)

*Primary Examiner*—Samir A. Ahmed
*Assistant Examiner*—Mehdi Rashidian
(74) *Attorney, Agent, or Firm*—Blakely, Sokoloff, Taylor & Zafman LLP

(57) ABSTRACT

A method of automatically generating an envelope of constraint points for a target region to optimize an inverse treatment plan by modifying the dose isocontour.

23 Claims, 13 Drawing Sheets

OTHER PUBLICATIONS

U.S. Appl. No. 11/242,366, Office Action dated Oct. 19, 2009, 17 pages.
U.S. Appl. No. 11/242,366, Restriction Requirement dated Aug. 7, 2009, 6 pages.
U.S. Appl. No. 11/242,366, Office Action dated Feb. 9, 2009, 7 pages.
U.S. Appl. No. 11/242,366, Restriction Requirement dated Dec. 22, 2008, 6 pages.
U.S. Appl. No. 11/145,121, Office Action dated Oct. 31, 2008, 30 pages.
Leksell, L., "The stereotactic method and radiosurgery of the brain", Acta Chirurgica Scandanavica 102 (1951), pp. 316-319.
Holder, A., "A tutorial on radiation oncology and optimization", in Greenberg, H.J., ed.: Tutorials on Emerging Methodologies and Applications in Operations Research. Kluwer Academic Press (2004).
Ferris, M., Lim, J., Shepard, D.: "An optimization approach for the radiosurgery treatment planning", SIAM Journal on Optimization 13 (2003), pp. 921-937.
Cheek, S., Holder, A., Fuss, M. Salter, B.: "The relationship between the number of shots and the quality of Gamma Knife Radiosurgeries." Technical Report 84, Department of Mathematics, Trinity University, San Antonio, TX (2004).
Rosen, I., Lane, R., Morrill, S., Belli, J.: "Treatment plan optimization using linear programming", Medical Physics 18 (1991), pp. 141-152.
Shepard, D., Ferris, M., Olivera, G., Mackie, T.: "Optimizing the delivery of radiation therapy to cancer patients", SIAM Review 41 (1999) pp. 721-744.
Bartolozzi, F., De Gaetano, A., DiLena, E., Marino, S., Nieddu, L., patrizi, G.: "Operational research techniques in medical treatment and diagnosis: a review." European Journal of Operations Research 121 (2000) pp. 435-466.
Holder, A.: "Radiotherapy treatment design and linear programming". Technical Report 70, Department of Mathematics, Trinity University, San Antonio, TX (2002).
Dantzig, G.B., Orden, A., Wolfe, P.: "The generalized Simplex method for minimizing a linear form under linear inequality restraints". Pacific Journal of Mathematics 5 (1955), pp. 183-195.
Paddick, I.: "A simple scoring ratio to index the conformality of radiosurgical treatment plans", Journal of Neurosurgery 93 (2000), pp. 219-222.
DeWyngaert, J.K., Noz, M.E., Ellerin, B., Kramer, E.L., Maguire, G.Q., Zeleznik, M.P., "Procedure for unmasking localization information from ProstaScint scans for prostate radiation therapy treatment planning", International Journal of Radiation Oncology, Biology, Physics, vol. 60, No. 2, pp. 654-662, 2004, Published by Elsevier.
D. Bechmann, N. Dubreuil, "Animation through space and time based on a space deformation model", The Journal of Visualization and Computer Animation, 4(3) 165-184, 1993.
Jay B. West et al., "Hybrid point-and-intensity-based deformable registration for abdominal CT images", Medical Imaging 2005, pp. 204-211.
Levoy, M., Fuchs, H., Pizer, S.M., Rosenman, J., Chaney, E.L., Sherouse, G.W., Interrante, V., Kiel, J., "Volume Rendering in Radiation Treatment Planning", Proc. First Conference on Visualization in Biomedical Computing, IEEE Computer Society Press, Atlanta, Georgia, May 1990, pp. 4-10.
Rudiger Westermann, Thomas Ertl, "Efficiently Using Graphics Hardware in Volume Rendering Applications", © 2000/2001 ACM. Reprinted with permission, from Proc. ACM SIGGRAPH 1998, pp. 169-178.
Klaus Engel, Martin Kraus, Thomas Ertl, "High-Quality Pre-Integrated Volume Rendering Using Hardware-Accelerated Pixel Shading", © 2001 ACM. Reprinted, with permission, from ACM SIGGRAPH/Eurographics Workshop on Graphics Hardware 2001, pp. 9-16, 121.
Jurgen Hesser et al., "Three Architectures for Volume Rendering", Eurographics '95, vol. 14, No. 3, 1995.
John Dooley, "Cyberknife® SRS System On-Target™ Treat Planning System, Clinical User's Guide", Accuray Incorporated, P/N. 017790, Rev. F, 2005.

\* cited by examiner

AUTOMATIC GENERATION OF AN ENVELOPE OF CONSTRAINT POINTS FOR INVERSE PLANNING

RELATED APPLICATION

This application claims the benefit of U.S. Provisional Application 60/692,606, filed Jun. 20, 2005.

TECHNICAL FIELD

This invention relates to the field of radiation treatment, and in particular, to inverse planning in radiation treatment.

BACKGROUND

Tumors and lesions are types of pathological anatomies characterized by abnormal growth of tissue resulting from the uncontrolled, progressive multiplication of cells, while serving no physiological function.

Pathological anatomies can be treated with an invasive procedure, such as surgery, but can be harmful and full of risks for the patient. A non-invasive method to treat a pathological anatomy (e.g., tumor, legion, vascular malformation, nerve disorder, etc.) is external beam radiation therapy. In one type of external beam radiation therapy, an external radiation source is used to direct a sequence of x-ray beams at a tumor site from multiple angles, with the patient positioned so the tumor is at the center of rotation (isocenter) of the beam. As the angle of the radiation source changes, every beam passes through the tumor site, but passes through a different area of healthy tissue on its way to the tumor. As a result, the cumulative radiation dose at the tumor is high and the average radiation dose to healthy tissue is low.

The term "radiotherapy" refers to a procedure in which radiation is applied to a target region for therapeutic, rather than necrotic, purposes. The amount of radiation utilized in radiotherapy treatment sessions is typically about an order of magnitude smaller, as compared to the amount used in a radiosurgery session. Radiotherapy is typically characterized by a low dose per treatment (e.g., 100-200 centiGray (cGy)), short treatment times (e.g., 10 to 30 minutes per treatment) and hyperfractionation (e.g., 30 to 45 days of treatment). For convenience, the term "radiation treatment" is used herein to mean radiosurgery and/or radiotherapy unless otherwise noted by the magnitude of the radiation.

Conventional isocentric radiosurgery systems (e.g., the Gamma Knife) use forward treatment planning. In forward treatment planning, a physician or medical physicist determines the radiation dose to be applied to a tumor and then calculates how much radiation will be absorbed by critical structures (i.e., vital organs) and other healthy tissue. There is no independent control of the two dose levels for a given number of beams, because the volumetric energy density at any given distance from the isocenter is a constant, no matter where the isocenter is located.

In inverse planning, in contrast to forward planning, the physician or medical physicist specifies the minimum dose to the tumor and the maximum dose to other healthy tissues independently, and the treatment planning software then selects the direction, distance, and total number and energy of the beams in order to achieve the specified dose conditions. Conventional treatment planning software packages are designed to import 3-D images from a diagnostic imaging source, for example, computerized x-ray tomography (CT) scans. CT is able to provide an accurate three-dimensional model of a volume of interest (e.g., skull or other tumor bearing portion of the body) generated from a collection of CT slices and, thereby, the volume requiring treatment can be visualized in three dimensions.

During inverse planning, a volume of interest (VOI) is used to delineate structures to be targeted or avoided with respect to the administered radiation dose. That is, the radiation source is positioned in a sequence calculated to localize the radiation dose into a VOI that as closely as possible conforms to the tumor requiring treatment, while avoiding exposure of nearby healthy tissue. Once the target (e.g., tumor) VOI has been defined, and the critical and soft tissue volumes have been specified, the responsible radiation oncologist or medical physicist specifies the minimum radiation dose to the target VOI and the maximum dose to normal and critical healthy tissue. The software then produces the inverse treatment plan, relying on the positional capabilities of the radiation treatment system, to meet the min/max dose constraints of the treatment plan.

FIG. 1 is a conceptual illustration of a graphical output of a treatment planning software displaying a slice of a CT image. The illustration of the CT image includes a pathological anatomy that is targeted for treatment, and well as a critical region that is positioned near the pathological anatomy. The treatment planning software enables the generation of a critical region contour around the critical region and a target region contour around the pathological anatomy. Conventionally, a user manually delineates points (e.g., some of the dots on the contour lines of FIG. 1) on the display that is used by the treatment planning software to generate the corresponding contours. While this may seem an easy task, such matching is difficult due to the three-dimensional nature and irregularities of the pathological and normal anatomies, and the limited number of beam positions available from the radiation beam source. Based on specified minimum dose to the target region and the maximum dose to the critical region, the treatment planning software generates a dose isocontour for the target region. The dose isocontour represents a given dose percentage (e.g., 60%, 70%, 80%, etc. of the maximum dose value) which is the specified prescription dose for the target region. Ideally, the dose isocontour should perfectly match the contour of the target region. In some cases, the dose isocontour generated by the treatment planning software is not optimal, and can include portions of the critical region, as illustrated in FIG. 1.

Two of the principal requirements for an effective radiation treatment system are homogeneity and conformality. Homogeneity is the uniformity of the radiation dose over the volume of the target (e.g., pathological anatomy such as a tumor, lesion, vascular malformation, etc.) characterized by a dose volume histogram (DVH). An ideal DVH for the pathological anatomy would be a rectangular function as illustrated in FIG. 2, where the dose is 100 percent of the prescribed dose over the volume of the pathological anatomy and zero elsewhere. A desirable DVH for a critical region would have the profile illustrated in FIG. 3, where the volume of the critical anatomical structures receives as little of the prescribed dose as possible.

Conformality is the degree to which the radiation dose matches (conforms) to the shape and extent of the target (e.g., tumor) in order to avoid damage to critical adjacent structures. More specifically, conformality is a measure of how much of the volume receiving at least the prescription (Rx) dose is contained within the target VOI. Conformality may be measured using a conformality index (CI)=total volume at >=Rx dose/target volume at >=Rx dose. Perfect conformality results in a CI=1. With conventional radiotherapy treatment, using treatment planning software, a clinician identifies a prescription dose for a target VOI, either as an absolute dose value (e.g., 3000 cGy), or as a percentage of maximum dose (e.g., 75%).

Ideally, the 100% dose isocontours for all of the slices should match the target region (e.g., tumor) over its three-dimensional volume. As discussed above, such matching is difficult due to the three-dimensional nature and irregularities of the pathological and normal anatomies. As such, a given inverse plan developed by the treatment planning software may be unsatisfactory because of lack of conformality, i.e., the dose isocontours representing a given dose percentage do not fit tightly enough to the boundary of the targeted treatment area (e.g., tumor or lesion). The conventional method to produce better conformality involves a manual procedure whereby a user manually delineates constraint points within a dose isocontour that encourages an optimization routine in the treatment planning software to bring the dose isocontour boundary closer to the surface of the target. However, such a manual task is time consuming and may not result in optimum conformality.

BRIEF DESCRIPTION OF THE DRAWINGS

The present invention is illustrated by way of example, and not by way of limitation, in the figures of the accompanying drawings.

DETAILED DESCRIPTION

Figure 1:
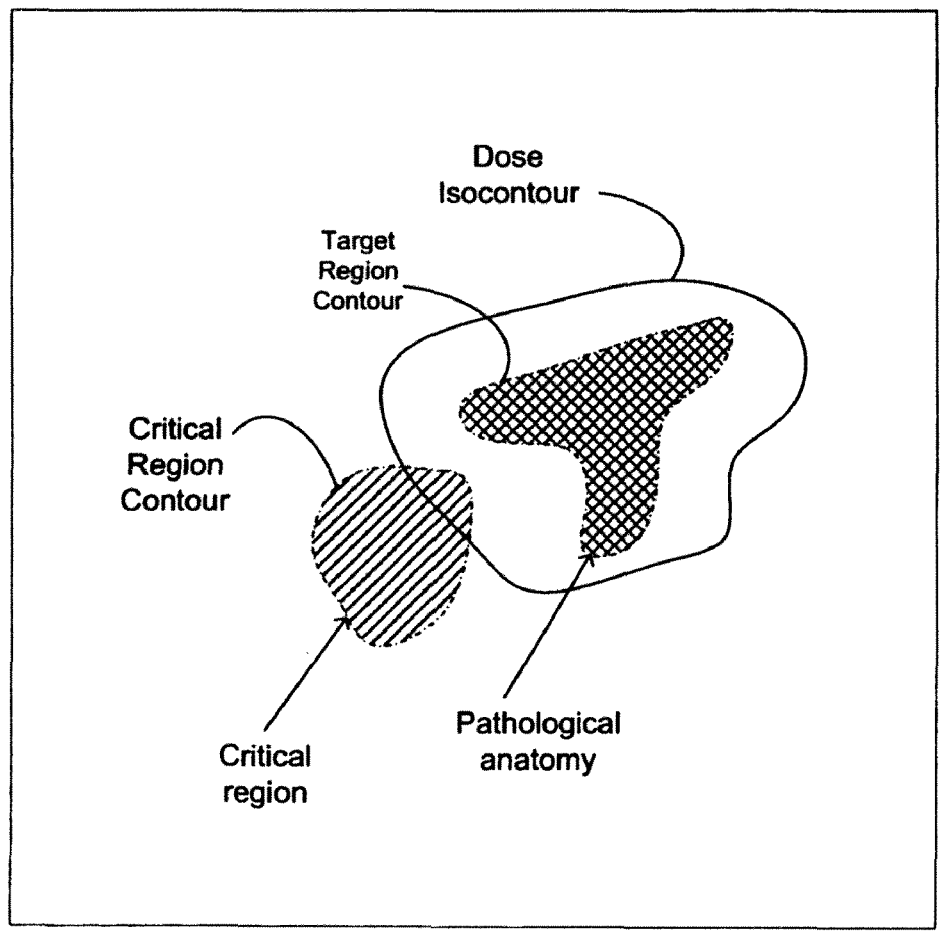
FIG. 1 illustrates a graphical output of a treatment planning software displaying a slice of a CT image.
Figure 2:
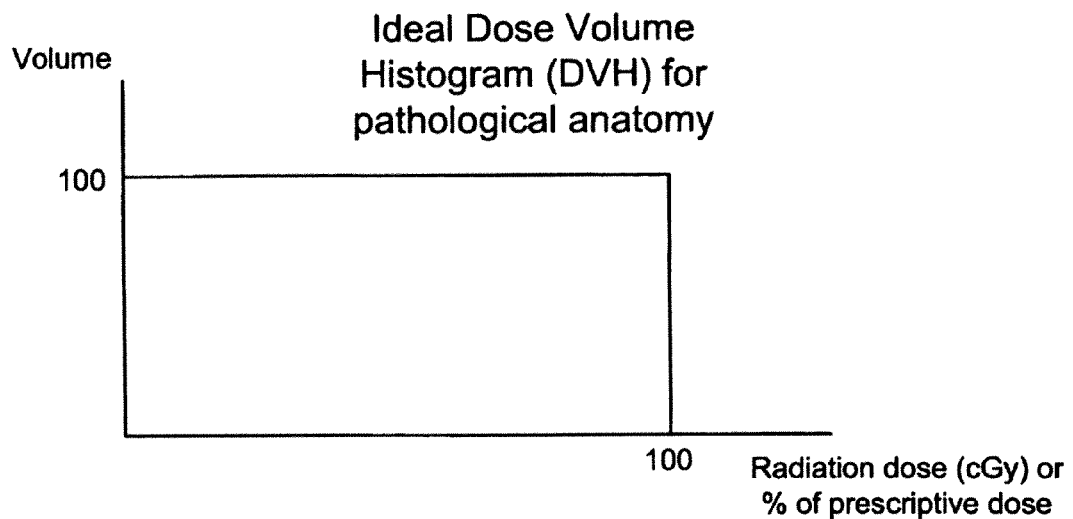
FIG. 2 is an ideal DVH for a pathological anatomy.
Figure 3:
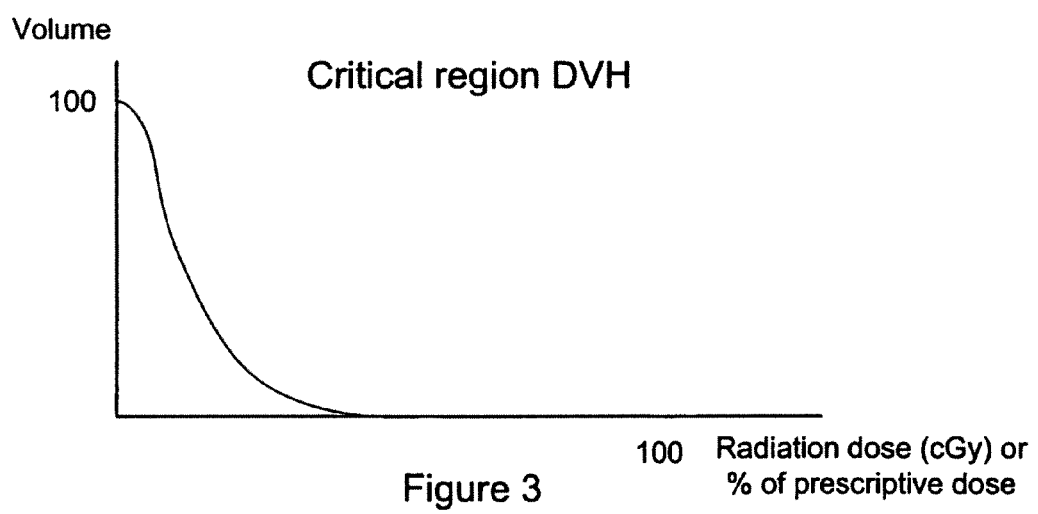
FIG. 3 is a desirable DVH for a critical region.

In the following description, numerous specific details are set forth such as examples of specific systems, components, methods, etc. in order to provide a thorough understanding of the present invention. It will be apparent, however, to one skilled in the art that these specific details need not be employed to practice the present invention. In other instances, well-known components or methods have not been described in detail in order to avoid unnecessarily obscuring the present invention.

Embodiments of the present invention include various steps, which will be described below. The steps of the present invention may be performed by hardware components or may be embodied in machine-executable instructions, which may be used to cause a general-purpose or special-purpose processor programmed with the instructions to perform the steps. Alternatively, the steps may be performed by a combination of hardware and software.

Embodiments of the present invention may be provided as a computer program product, or software, that may include a machine-readable medium having stored thereon instructions, which may be used to program a computer system (or other electronic devices) to perform a process. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or other type of medium suitable for storing electronic instructions.

Embodiments of the present invention may also be practiced in distributed computing environments where the machine-readable medium is stored on and/or executed by more than one computer system. In addition, the information transferred between computer systems may either be pulled or pushed across the communication medium connecting the computer systems, such as in a remote diagnosis or monitoring system. In remote diagnosis or monitoring, a user may utilize embodiments of the present invention to diagnose or monitor a patient despite the existence of a physical separation between the user and the patient. In addition, the treatment delivery system may be remote from the treatment planning system.

Embodiments of a method are described to generate an envelope of constraint points during treatment planning for radiation treatment. In one embodiment, an envelope of constraint points may be generated based on the three-dimensional, anatomical shape of the pathological anatomy. During inverse planning, one method to optimize the treatment plan involves making changes in the plan parameters, such as the number, placement, and length of activation of the treatment radiation beams, so that the accepted plan produces a dose isocontour that closely matches the contour of the pathological anatomy. The envelope of constraint points may contain at least one set of dose constraint points corresponding to either an exterior surface or an interior surface of the pathological anatomy. For example, a set of dose constraint points may be located near the outer surface of the pathological anatomy, near the inner surface of the pathological anatomy, or both. The set of exterior constraint points may be generated by a three-dimensional dilation algorithm, and the set of interior constraint points may be generated by a three-dimensional erosion algorithm. The one or more sets of dose constraint points that are automatically generated by the treatment planning software may be used during treatment planning as inputs to the optimization algorithm in order to produce a maximally conformal dose isocontour for the pathological anatomy.

In one embodiment, the automatically generated constraint points may be assigned an initial weight of approximately zero, so that the constraint points are not involved in the initial iterations of inverse planning. Then, for the current dose isocontour that is generated for the pathological anatomy, if an external constraint point is inside the current dose isocontour, a dose weight may be assigned to that constraint point (i.e., a substantially non-zero dose weight) as a way of "activating" the constraint point. In subsequent iterations of treatment planning, the "active" constraint points are utilized to modify the current dose isocontour and generate an optimized dose isocontour. Analogously, if an internal constraint point is outside the current dose isocontour, a dose weight may be assigned to that constraint point (i.e., substantially non-zero dose weight). In subsequent iterations of treatment planning, the "active" constraint points are utilized to generate an optimized dose isocontour. It should be noted that although discussed at times herein in regards to inverse planning, the methods herein may also be used with a mixed planning approach in which part of the treatment dose is generated by isocenters placed using forward planning and part generated by individual beams during inverse planning. It should also be noted that the methods and apparatus are discussed herein in relation to CT imaging only for ease of explanation. The methods and apparatus discussed herein may also be used to generate VOIs from other types of medical diagnostic images (anatomical and/or functional), for example, magnetic resonance (MR), ultrasound (US), nuclear medicine (NM), PET/SPECT, etc. In addition, the "targets" discussed herein may be an anatomical feature(s) of a patient such as a pathological or normal anatomy and may include one or more non-anatomical reference structures.

Figure 4:
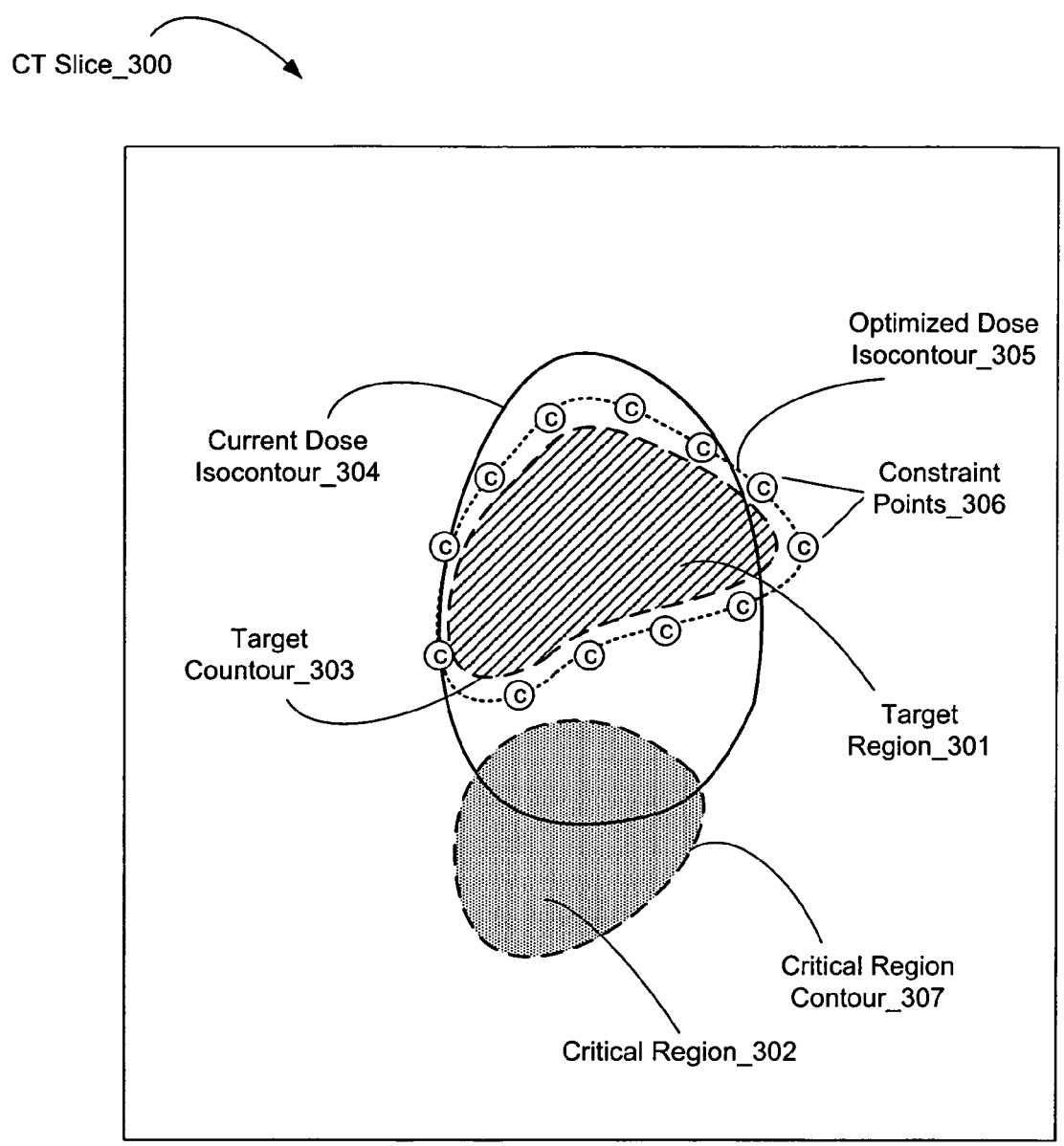
FIG. 4 illustrates the optimization of a current dose isocontour based on the automatic generation of an envelope of constraint points.

FIG. 4 illustrates an example of a two-dimensional CT slice 300 through a VOI (i.e., a three-dimensional volume containing a dose isocontour region, target region, and critical region), which may represent the displayed output (e.g., CT slice with graphical tool overlay) from a treatment planning software. FIG. 4 is shown to describe one embodiment of optimizing a current dose isocontour to a desired dose isocontour by utilizing an envelope of constraint points that are automatically generated with respect to the anatomical shape of the pathological anatomy, by the treatment planning software. The two-dimensional slice 300 includes a critical region 302 having a critical region contour 307, a target (e.g., pathological anatomy) region 301 having a target contour 303, a current dose isocontour 304 that encompasses a current dose region, and an optimized dose isocontour 305 that encompasses a desired dose region. In one embodiment, current dose isocontour 304 represents a given dose percentage (e.g., 60%, 70%, 80%, etc.) of the maximum dose for the target region 301. Although a critical region is discussed herein, in an alternative embodiment, the optimized dose isocontour 305 may be automatically generated without the existence and/or input of a critical region.

In one embodiment, the contours of FIG. 4 may be generated using inverse planning in which dose constraints such as the minimum dose to target region 301 and the maximum dose to critical region 302 are specified by a user. Based on the minimum and maximum doses, the treatment planning software selects the direction, distance, and total number and energy of the beams that are used to implement the treatment plan. In particular, a radiation source is positioned in a sequence calculated to localize the radiation dose into the VOI that as closely as possible conforms to target region 301, while avoiding exposure of regions outside of target region 301, such as critical region 302. The treatment planning software then produces an inverse treatment plan, relying on the positional capabilities of the radiation treatment system, to meet dose constraints as closely as possible.

The treatment planning software also performs a radiation dose calculation for the VOI displayed in CT slice 300. The treatment planning software considers a set of beams that are directed at target region 301. In one embodiment, the treatment planning software is used with a radiation source that has a collimator that defines the width of the set of beams that is produced and determines, for example, the number of beams, their sizes (e.g., as established by the collimator), their positions and orientations, as well as the amount of radiation from each beam. The total amount of radiation exiting the collimator for one beam is defined in terms of Monitor Units (MU). Because the intensity of the radiation source is constant, the MU is linearly related to the amount of time for which the beam is enabled. The radiation dose absorbed due to a given beam (in units of cGy) by tissue in the path of the beam is also linearly related to the MU. The absorbed dose related to a beam is also affected by the collimated size of the beam, the amount of material between the collimator and the calculation point, the distance of the collimator from the calculation point, and the distance of the calculation point from the central axis of the beam.

Figure 9:
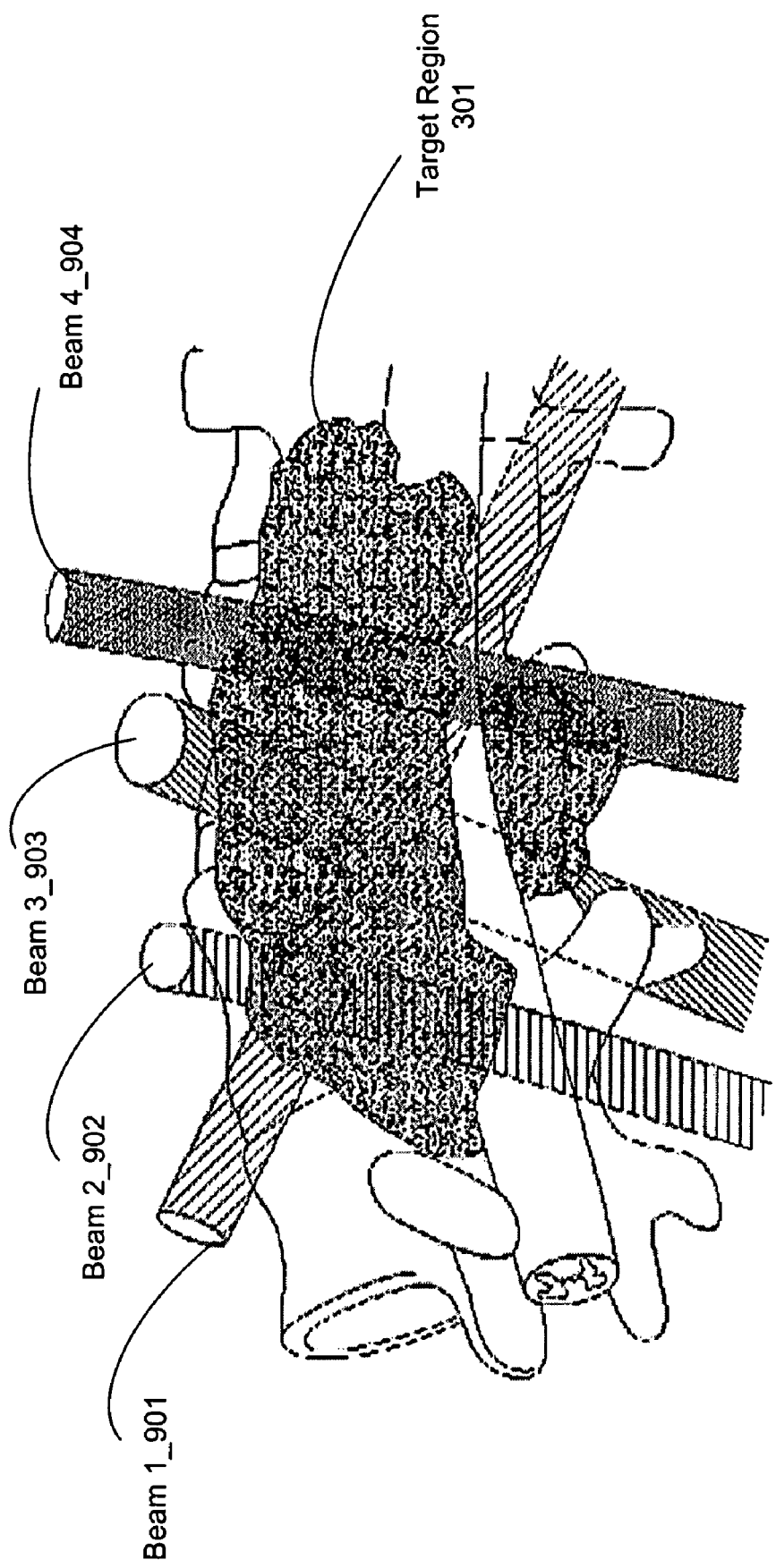
FIG. 9 illustrates a two-dimensional perspective of radiation beams originating from a radiation treatment system directed at a pathological anatomy.

FIG. 9 illustrates a perspective of radiation beams originating from a radiation treatment system directed at target region 301 (i.e., the pathological anatomy). It should be noted that four beams, beam_1 901, beam_2 902, beam_3 903, and beam_4 904 are illustrated in FIG. 9 only for ease of discussion and that an actual treatment plan may include more, or fewer, than four beams. Moreover, the four beams are representative of conformal planning, in which each beam passes through various points within target region 301. In conformal planning, some beams may or may not intersect or converge at a common point, and although the four beams appear to intersect in the perspective of FIG. 9, the beams may not intersect in their actual three-dimensional space. The radiation beams need only intersect with the target volume and do not necessarily converge on a single point, or isocenter, within the target. The initial beam weights may be a default beam weight determined by the operator or the treatment planning software. The initial beam weights may also be influenced by the prescribed radiation dose to be delivered to target region 301. For example, if a total prescribed dose of 3500 cGy is set for target region 301, the treatment planning software would automatically determine the beam weights for each beam to balance conformality and homogeneity to achieve that prescribed dose as closely as possible.

Current dose isocontour 304 exemplifies the undesirable shape that can result initially during the treatment plan optimization process. As shown, the current dose isocontour 304 does not match the shape of target region 301 very closely, and in particular, overlaps into a portion of critical region 302. One goal of treatment planning is to have the dose isocontour match the shape of the target region as closely as possible, as exemplified by optimized dose isocontour 305. In one embodiment, current dose isocontour 304 can be optimized to the shape of desired dose isocontour 305 by utilizing constraint points 306 that are outlined around an exterior surface of target region 301. It should be noted that because CT slice 300 is a two-dimensional representation of a three-dimensional volume (i.e., target region 301 is a slice of a pathological anatomy volume), constraint points 306 are actually positioned around the entire three-dimensional surface of the pathological anatomy. In one embodiment, constraint points 306 are generated around an outer surface of target region 301 using a three-dimensional image erosion-dilation algorithm, such as a rolling ellipsoid algorithm.

One embodiment of a rolling ellipsoid algorithm involves the rolling of a non-symmetric ellipsoid at each boundary point of a pathological anatomy. The main aspects of the algorithm include (a) calculating an ellipsoid mask volume; (b) calculating a target VOI mask volume; (c) detecting all the boundary points from the target VOI mask volume; (d) updating the target VOI mask volume for each boundary point; and (e) detecting contours of the new eroded and/or dilated surfaces. In step (a) (calculating an ellipsoid mask volume), a three-dimensional mask volume is calculated based on the user's input of the distance to be dilated or eroded. Each voxel inside the mask volume has two possible values: 0, and 1. All the voxels that have distances larger than the distance to be eroded or dilated are assigned with 0; otherwise, voxels are assigned with 1. In step (b) (calculating a target VOI mask volume), another three-dimensional mask volume is calculated based on the target VOI. A value of 1 is assigned to all the voxels that are inside the target VOI, and 0 is assigned to all the voxels that are outside the target VOI. In step (c) (detecting all the boundary points from the target VOI mask volume), all boundary points of the target VOI are detected based on the neighboring voxels of each point in the target VOI mask volume. If a point has at least one neighboring voxel that has a mask value of 1, and at least one neighboring voxel has a mask value of 0, the point is considered as a boundary point. In step (d) (updating the target VOI mask volume for each boundary point), for each boundary point of the target VOI mask volume, the mask volume of the ellipsoid is positioned at the boundary point with the center of the ellipsoid aligned with the boundary point. Then, all the voxels that are covered by the ellipsoid mask are updated with the value from the ellipsoid mask. In step (e) (detecting contours of the new eroded and/or dilated surfaces), geometrical contours are then detected from the final target VOI mask volume, to form the dilated and/or eroded surfaces. Three-dimensional image erosion-dilation algorithms are known in the art; accordingly, a detailed description is not provided herein.

Constraint points 306 are automatically generated based on the anatomical shape of target region 301 and may be spaced evenly apart around target region 301. Constraint points 306 may have the type, "less than or equal to" and a maximum dose value, with the weights of constraint points being constant, or determined by a distance from the point to the optimized dose isocontour 305. In the latter case, the weights for constraint points may be assigned in real-time during inverse planning.

In an embodiment in which an iterative planning algorithm is used, the weights of all constraint points 306, when automatically generated, are initially set to approximately zero. Therefore, they do not participate in the first iteration of inverse planning. After the treatment planning software runs one or more iterations, the current dose isocontour 304 is generated based on the current dose volume. For each of the constraint points 306, if the constraint point is inside the current dose isocontour 304, the distance from that point to the current dose isocontour 304 is calculated. A weight, based on the magnitude of that distance, is assigned to that constraint point. If a constraint point is not inside the current dose isocontour 304, its weight remains zero or approximately zero. After each constraint point is evaluated, the constraint points 306 inside the dose isocontour 304 are activated (with a substantially non-zero weight value), and included as part of the next iteration in the treatment plan optimization process. This process may be repeated as necessary until an acceptable result is generated (e.g., forming optimized dose isocontour 305), or the planning process is terminated by the operator.

Figure 5:
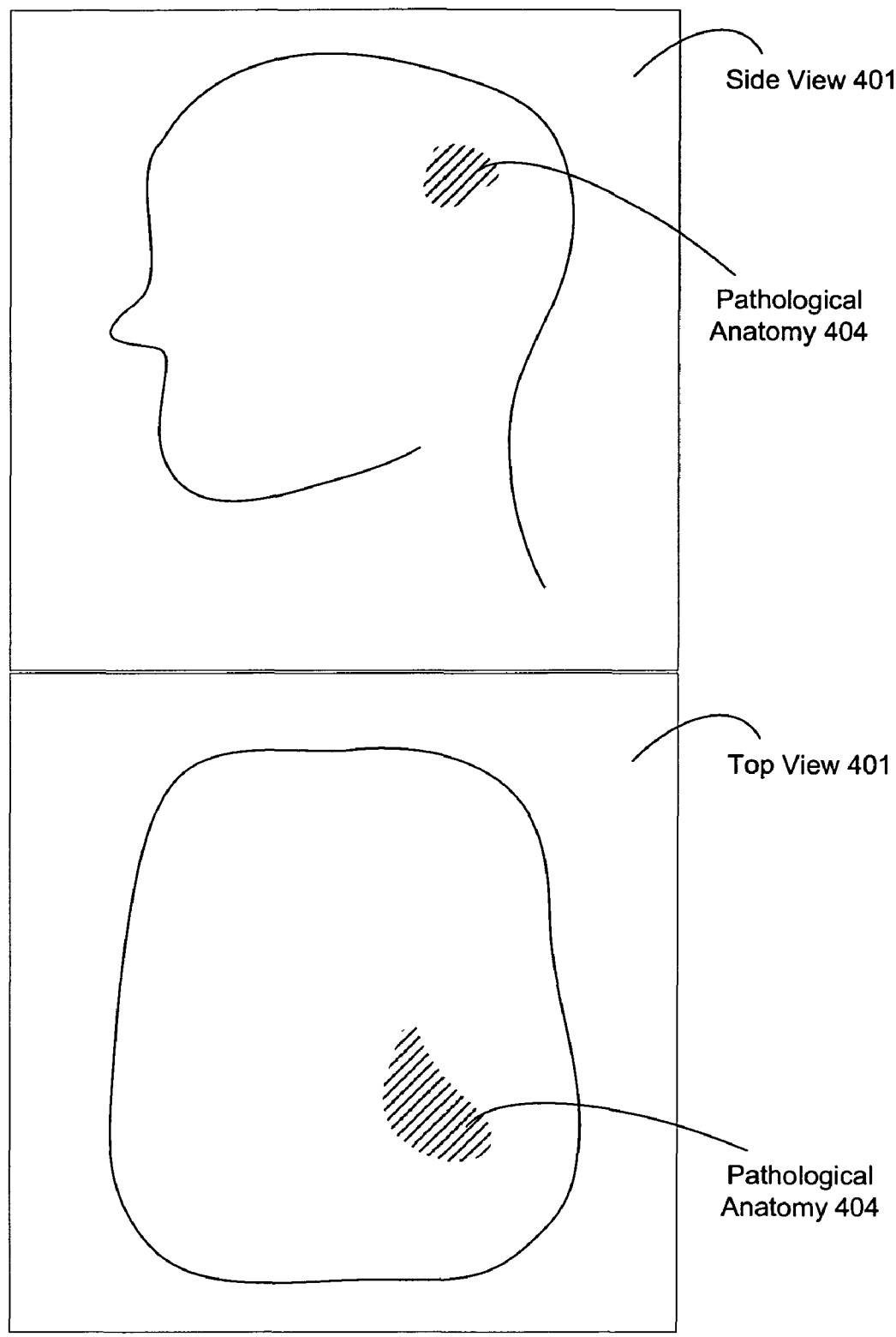
FIG. 5 illustrates different CT scan views of an intracranial pathological anatomy.

In inverse planning, the operator or physician interfaces with a treatment planning software program to develop the treatment plan for the patient. A medical image, such as a CT scan, is used to define a volume of interest that includes for example, a target region or a critical region. As such, two-dimensional images are used to develop a treatment plan, even though the pathological anatomy is actually a three-dimensional structure. FIG. 5 illustrates different CT scan views of an intracranial pathological anatomy 404. CT slice 401, which represents a side view of the intracranial region, shows how pathological anatomy 404 has a different shape and size relative to CT slice 402, which represents a top view of the intracranial region. During inverse planning, the operator or physician may use one or both of the orientations shown in FIG. 5 to define a VOI for treatment. In alternative embodiments, other orientations of the intracranial region may be used.

Figure 6A:
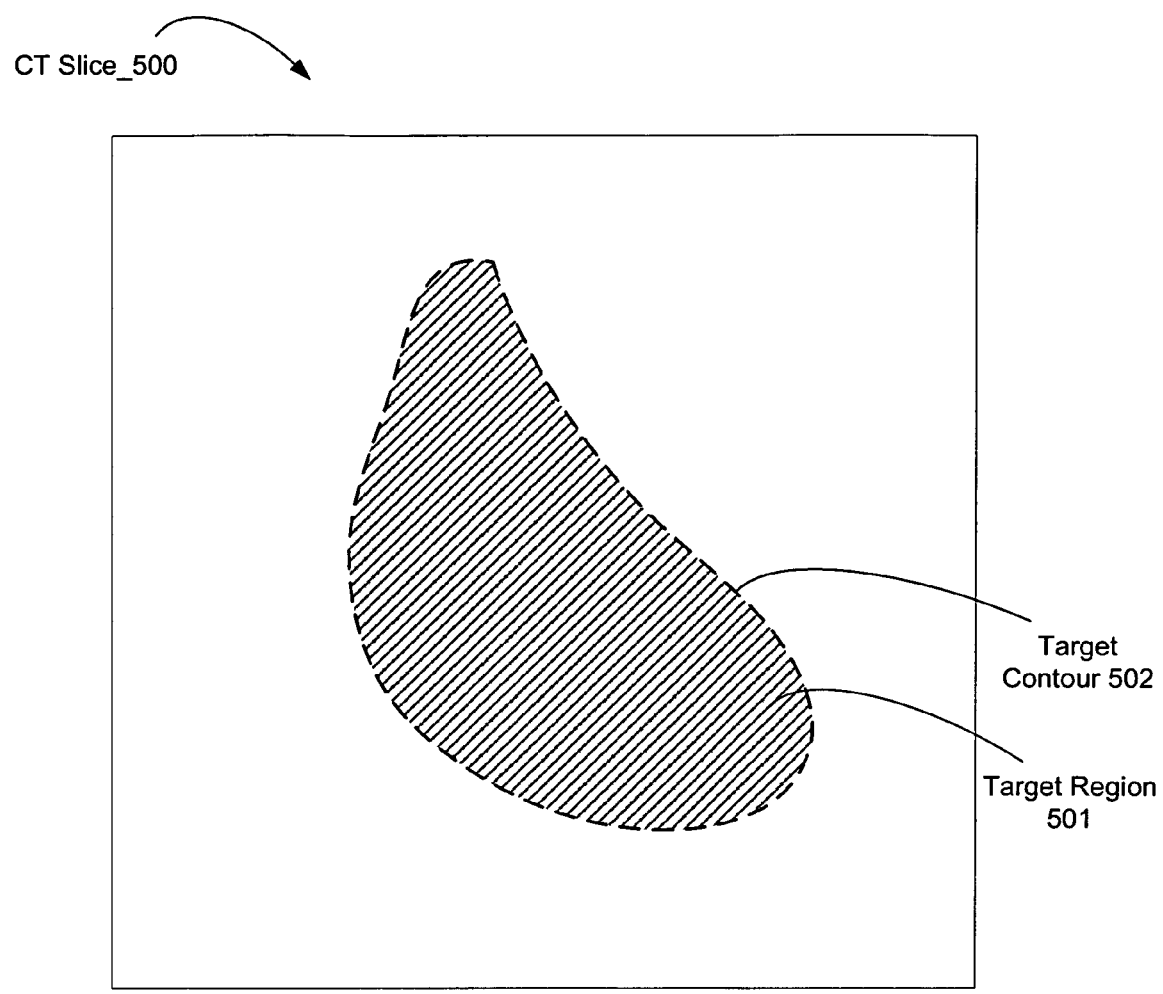
FIG. 6A illustrates a CT slice that contains the VOI target region and the target region contour that has been delineated during the initial stages of treatment planning.
Figure 6B:
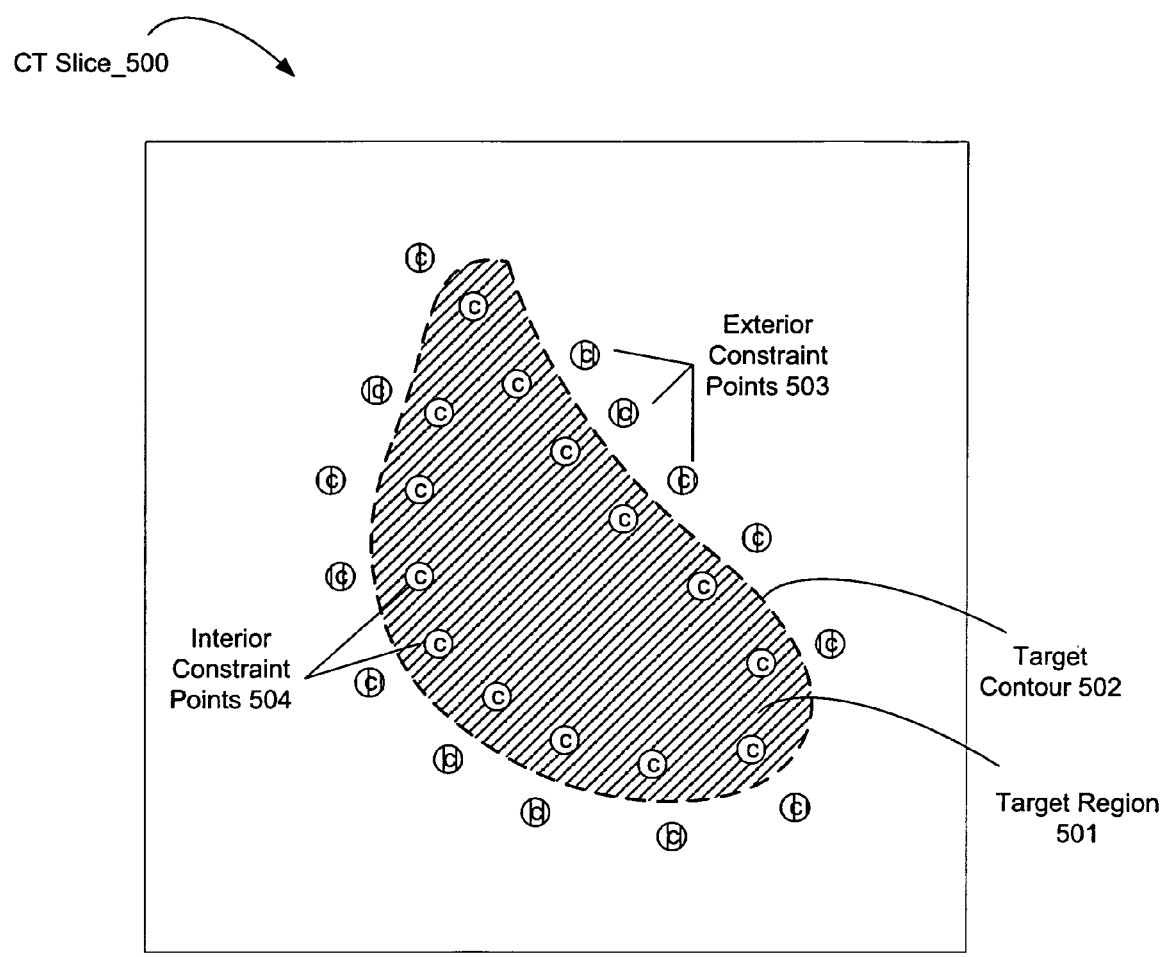
FIG. 6B illustrates an automatic generation of two sets of constraint points based on the anatomical shape of target region.

A method to optimize a current dose isocontour during treatment planning for pathological anatomy 404 is described with respect to FIGS. 6A-6D. FIG. 6A illustrates a CT slice that contains the VOI target region 501 (i.e., pathological anatomy 404) and the target region contour 502 that has been delineated during the initial stages of treatment planning. Target region contour 502 (represented by the segment line around target region 501) may be manually formed by a user or automatically generated by the treatment planning software. FIG. 6B illustrates an automatic generation of two sets of constraint points based on the anatomical shape of target region 501. In one embodiment, a rolling ellipsoid algorithm is used to create an exterior surface and an inner surface with respect to target region 501. For example, a dilation algorithm may be used to create the exterior surface and an erosion algorithm may be used to create the interior surface, based on the volume of target region 501. A first envelope of constraint points is positioned along the exterior surface, represented by exterior constraint points 503. A second envelope of constraint points is positioned along the interior surface, represented by interior constraint points 504. In one embodiment, each constraint point of exterior constraint points 503 may be spaced substantially equal to each other along the exterior surface. Similarly, each constraint point of the interior constraint points 504 may be spaced substantially equal to each other along the interior surface. In an alternative embodiment, the constraint points may be spaced unevenly along either the interior or exterior surfaces. Because the envelope of constraint points are based on the anatomical shape of the pathological anatomy, the exterior constraint points 503 appear as a larger version of target region 501 and interior constraint points 504 appear as a smaller version of target region 501 when viewed on CT slice 500.

Figure 7:
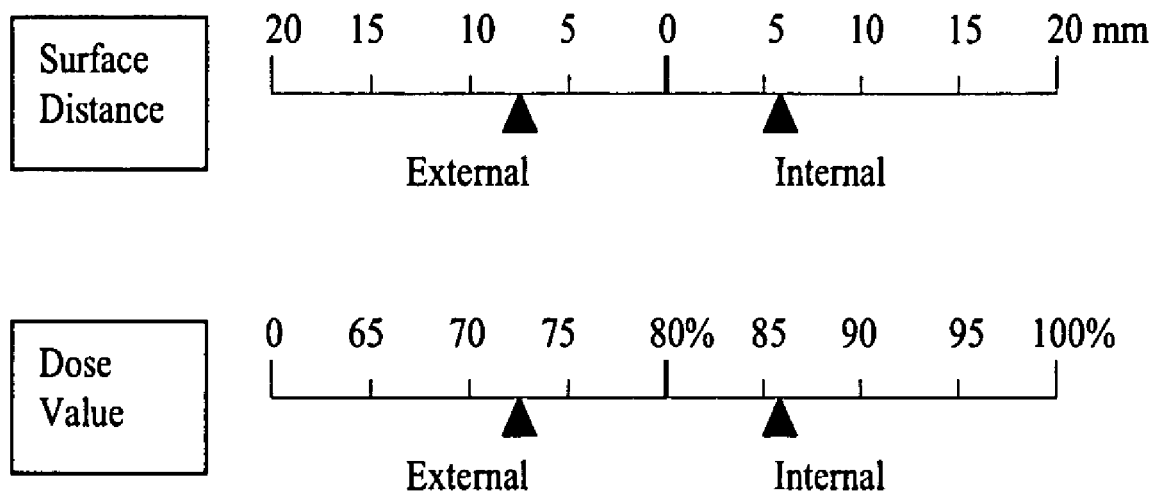
FIG. 7 illustrates one embodiment of user defined parameters for the envelope of constraint points.

Although the exterior constraint points 503 and interior constraint points 504 are automatically generated by the treatment planning software, the user or operator may control one or more parameters related to the properties for the envelope of constraint points. For example, the treatment planning software may include user controls for defining distances from the external and internal surfaces of target region 501. The user may also assign the dose values for external constraint points 503 and/or internal constraint points 504 in terms of a percentage relative to a percentage of current maximum dose. The controls may be represented on a display screen as part of a user interface with the treatment planning software. FIG. 7 illustrates one embodiment of user defined parameters for the envelope of constraint points. One parameter includes a distance of each constraint point relative to the surface of the target region, represented in embodiment by a sliding meter for the exterior constraint points and the interior constraint points. For example, a distance between a constraint point from the exterior constraint points 503 to the outer surface of target region 501 may be defined. Analogously, a distance between a constraint point from the interior constraint points 504 to the inner surface of the target region may be defined by the user. In one embodiment, the exterior distance may be substantially equal to the interior distance. In an alternative embodiment, the exterior distance may be different than the interior distance.

FIG. 7 also illustrates that radiation dose value is another parameter that may be defined by the user. The dose values for the external constraint points 503 and the internal constraint points 504 may be defined with respect to the prescription dose to the target region, represented in one embodiment by a meter. For example, the prescribed dose for target region 501 may be 80% and 2400 cGy (where 3000 cGy is the maximum dose). The dose value for the external constraint points 503 would be a value between the prescribed dose and 0% (e.g., 73%), and the dose value for the internal constraint points 504 would be a value between the prescribed dose and 100% (e.g., 86%). The prescription dose of 80% and 2400 cGy is provided by way of example only, and in alternative embodiments, the prescription dose may be any value specified by the operator or physician.

Figure 6C:
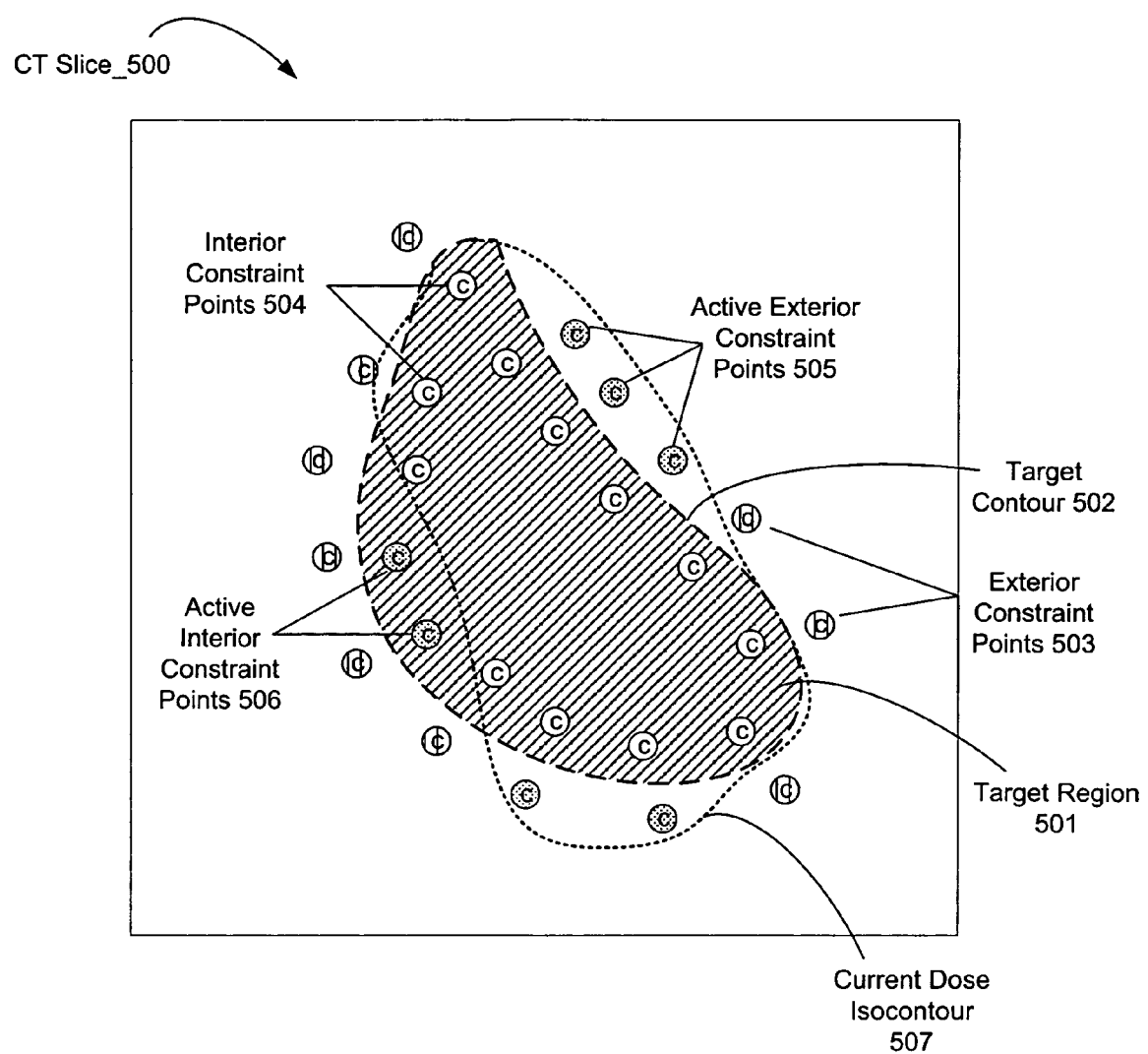
FIG. 6C illustrates a current dose isocontour based on one or more initial constraints specified by the user.

The treatment planning software generates a current dose isocontour 507, as illustrated in FIG. 6C, based on one or more initial constraints specified by the user, such as minimum dose to target region 501 and maximum dose to a critical region (not shown), but without regard for the exterior constraint points 503 and interior constraint points 504. In an iterative treatment planning process, the weights of all the exterior constraint points 503 and interior constraint points 504 are initially set to approximately zero (i.e., no weight or almost no weight) when automatically generated by the treatment planning software and as such, the constraint points do not participate in the first iteration of the treatment planning process. This first iteration performed by the treatment planning software may generate a shape for the current dose isocontour 507 that does not closely match the shape of target region 501, in which portions are either significantly outside or inside relative to target region 501. In a subsequent iteration of the treatment planning process, constraint points from the exterior constraint points 503, the interior constraint points 504, or both may be activated to manipulate current dose isocontour 507 to fit target region 501 more closely.

In one embodiment, whether a constraint point is activated may be determined by its position relative to a corresponding point on the current dose isocontour 507. For example, one condition for activation may be whether a constraint point from the external constraint points 503 is inside the current dose isocontour 507. FIG. 6C illustrates active exterior constraint points 505, which are positioned inside of current dose isocontour 507. The treatment planning software calculates a distance from each of active exterior constraint points 505. A dose weight, based on the magnitude of that distance, is then assigned to active exterior constraint points 505. The dose weight to active exterior constraint points 505 may be substantially similar or different, based largely on the distance to current dose isocontour 507. The remaining exterior constraint points 503 remain with an approximate zero weight.

Another condition for activation may be whether a constraint point from the interior constraint points 504 is outside the current dose isocontour 507. FIG. 6C also illustrates active interior constraint points 506, which are positioned inside of current dose isocontour 507. The treatment planning software calculates a distance from each of active interior constraint points 506. A dose weight, based on the magnitude of that distance, is then assigned to active interior constraint points 506. The dose weight to active interior constraint points 506 may be substantially similar or different, based largely on the distance to current dose isocontour 507. The remaining interior constraint points 504 remain with an approximate zero weight. During the next iteration of the treatment planning process, active exterior constraint points 505 and active interior constraint points 506, which now have a non-zero weight value, are used to produce an improved result for the current dose isocontour 507.

Figure 6D:
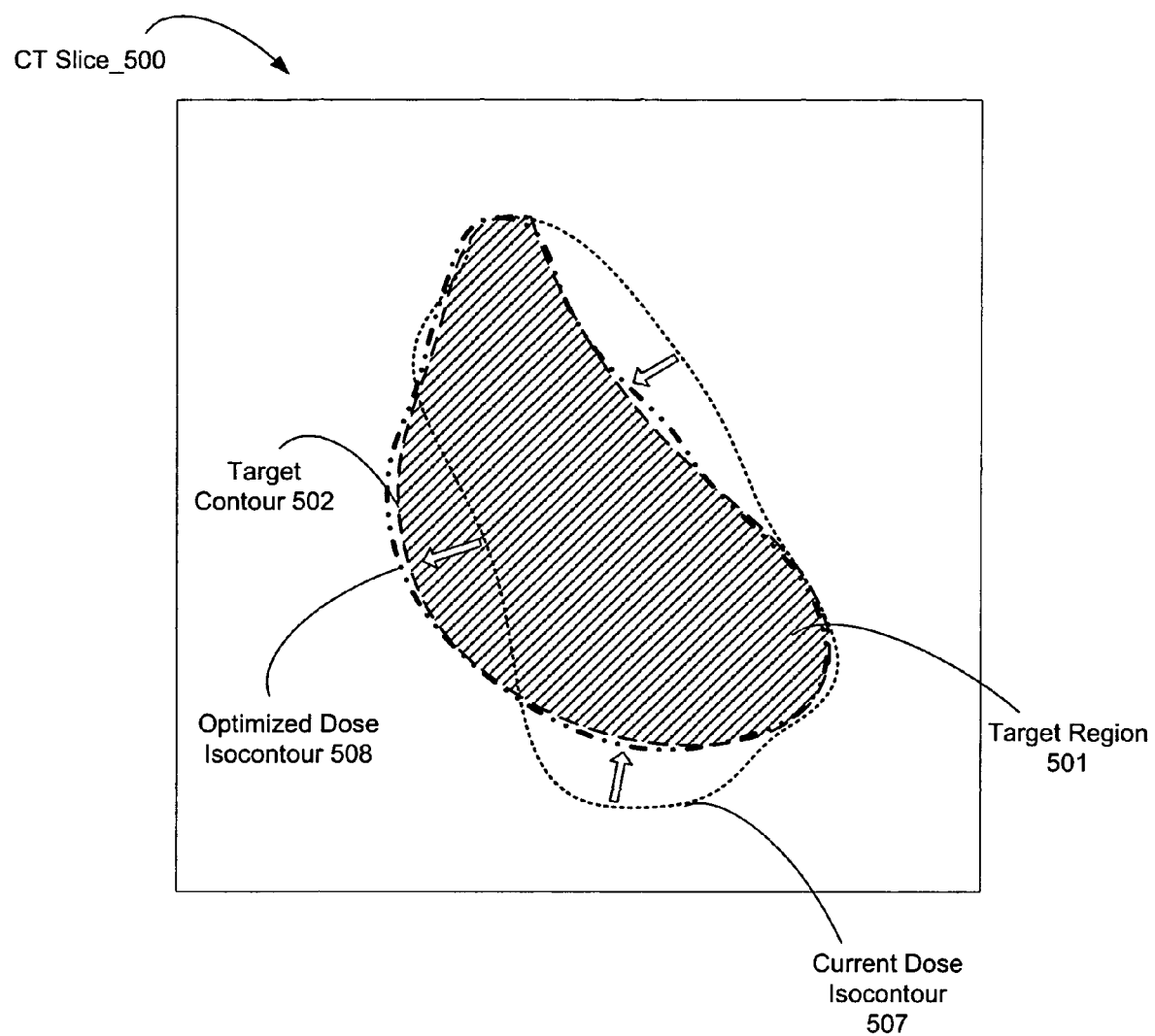
FIG. 6D illustrates the improvement of the shape of the current dose isocontour to an optimized dose isocontour.

FIG. 6D illustrates the improvement of the shape of current dose isocontour 507 to optimized dose isocontour 508 relative to the shape of target region 501. Because the treatment planning process has been described with respect to an iterative process, optimized dose isocontour 508 may be the result of one or more iterations based on activating one or more constraint points from the exterior constraint points 503 and interior constraint points 504. The treatment planning process using the automatically generated envelope of constraint points may be repeated as often as desired until an acceptable treatment plan results, or until the planning process is terminated by the user.

The treatment plan optimization process described with respect to FIGS. 6A-6D utilizes two sets of constraint points—exterior constraint points 503 and interior constraint points 504. It is noted that, in an alternative embodiment, the manipulation of current dose isocontour 507 may be accomplished with the use of only one set of constraint points. For example, the treatment planning software may generate exterior constraint points 503 only. That is, a rolling ellipsoid algorithm may be used to form a dilated surface based on the anatomical shape of target region 501 to position exterior constraint points 503. The exterior constraint points 503 may have the condition, "less than or equal to" and a maximum dose value. For any constraint points inside of current dose isocontour 507, they may be activated as described above with respect to FIG. 6C and included in the next iteration of treatment planning. Analogously, the treatment planning software may generate interior constraint points 504 only. The rolling ellipsoid algorithm may be used to form an eroded surface based on the anatomical shape of target region 501 to position interior constraint points 504. The interior constraint points 504 may have the condition, "greater than or equal to" and a minimum dose value. For any constraint points outside of current dose isocontour 507, they may be activated as described above with respect to FIG. 6C and included in the next iteration of treatment planning.

Figure 8:
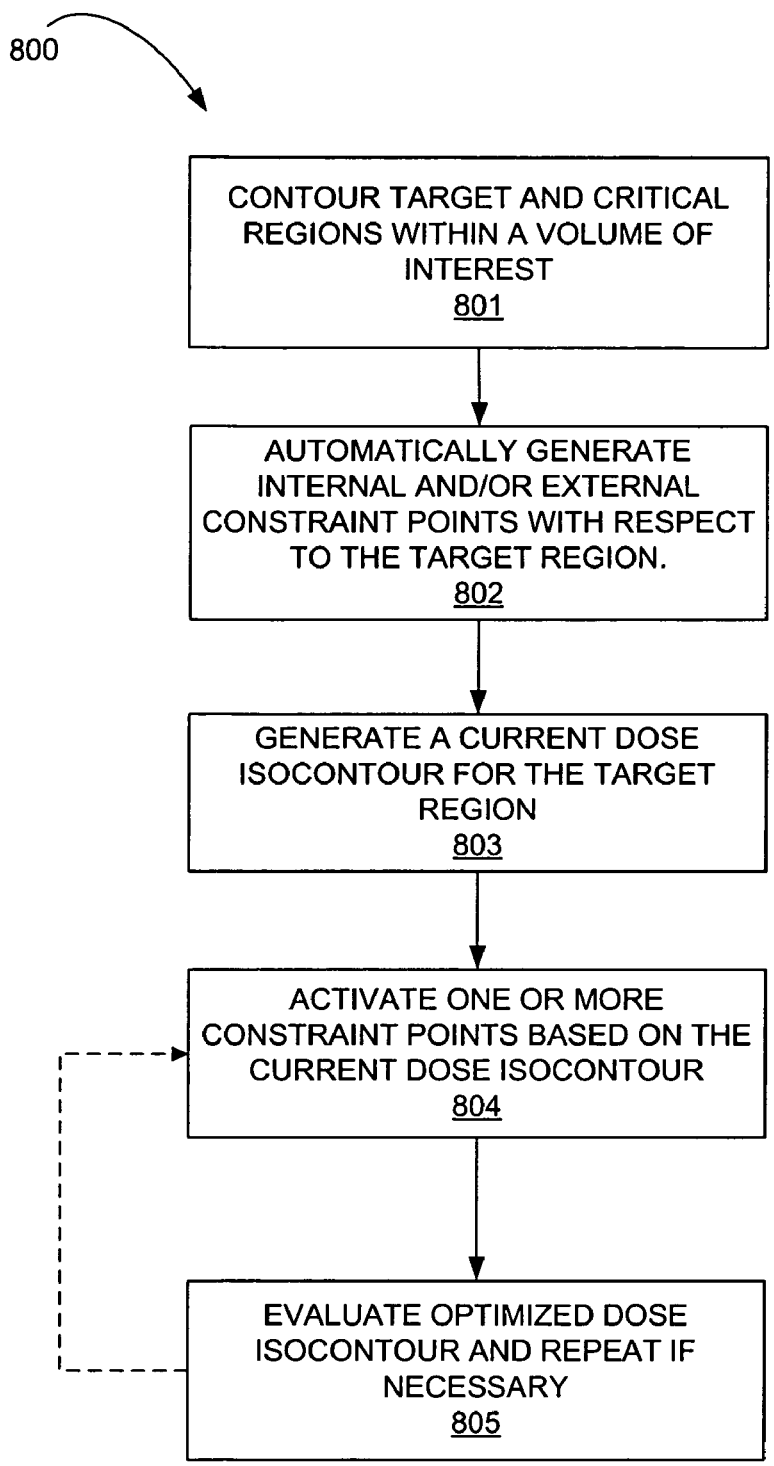
FIG. 8 is a flowchart describing one embodiment of a method of inverse treatment planning.

FIG. 8 is a flowchart 800 describing one embodiment of a method of inverse treatment planning. Flowchart 800 is described with respect to optimizing a current dose isocontour for a target region (e.g., corresponding to a pathological anatomy), but the method of the present invention is not so limited and may be generally applied to the optimization of a treatment plan for the delivery of radiation dose to any pathological anatomies in a patient. In one embodiment, anatomical data of a pathological anatomy is obtained by acquiring an anatomical image (e.g., CT) to form a three-dimensional view of the pathological anatomy and the surrounding tissue. An exemplary CT scan is the axial slices of a patient's intracranial region illustrated in FIG. 5. The CT image displays the location and size of the pathological anatomy (e.g., 404) and its surrounding tissue, including critical structures.

In examining the anatomical image on a display screen, the operator can identify a target region for radiation treatment, and the presence of any critical regions near the target region for consideration so that the critical regions receive as little radiation as possible. In step 801, the operator delineates the target and critical regions by contouring these regions on the display screen (e.g., target region contour 502 corresponding to target region 501). The operator can now input one or more treatment planning constraints to maximize conformality and homogeneity. One type of treatment planning constraint is minimum dose for the target region and maximum dose for the critical region. Another type of treatment planning constraint relates to the radiation beams for use in the treatment. For example, a starting beam weight, width, or orientation for all the beams that are to be used in the treatment may be assigned values. In alternative embodiments, the operator may input other types of treatment planning constraints.

In step 802, the treatment planning software generates one or more sets of constraint points based on the anatomical shape of target region. In one embodiment, a rolling ellipsoid algorithm may be used to create an exterior surface and an inner surface with respect to the target region. For example, a dilation algorithm may be used to create the exterior surface and an erosion algorithm may be used to create the interior surface, based on the volume of the target region. A first envelope of constraint points (e.g., exterior constraint points 503) are positioned along the exterior surface. A second envelope of constraint points (e.g., interior constraint points 504) are positioned along the interior surface. Although the exterior constraint points and interior constraint points are automatically generated by the treatment planning software, the user or operator may control one or parameters related to the properties for the envelope of constraint points. For example, the treatment planning software may include user controls for defining distances from the external and internal surfaces of target region, as well as dose values for the external constraint points and/or the internal constraint points in terms of a percentage relative to a percentage of current dose isocontour. In one embodiment, the envelope of constraint points may be assigned an initial weight of approximately zero.

The treatment planning software generates a current dose isocontour (e.g., 507) based on initial inputs specified by the user, step 803, such as minimum dose to the target region, but without the influence of the exterior constraint points or interior constraint points. The first iteration of the treatment plan performed by the treatment planning software may generate an unacceptable shape for the current dose isocontour, in which portions are either significantly outside or inside relative to the target region. In a subsequent iteration of the treatment planning process, constraint points from the exterior constraint points, the interior constraint points, or both may be activated to manipulate the current dose isocontour to fit the target region more closely, step 804.

In one embodiment, the activation of a constraint point may be determined by its position relative to a corresponding point on the current dose isocontour. For example, one condition for activating a constraint point may be whether a constraint point from the external constraint points is inside the current dose isocontour. Another condition for activating may be whether a constraint point from the interior constraint points is outside the current dose isocontour. If one of these conditions exists, the treatment planning software calculates a distance from each of the active constraint points (e.g., active exterior constraint points 505 and active interior constraint points 506). A weight, based on the magnitude of that distance, is then assigned to the active constraint point. The remaining non-active constraint points remain with an approximate zero weight. During the next iteration of the treatment planning process, the active constraint points, which now have non-zero weight values, are used to produce an optimized dose isocontour (e.g., 508). Because the treatment planning process is iterative, the optimized dose isocontour may be evaluated, and the activation process may be repeated to activate other constraint points, step 806. The final optimized dose isocontour may be the result of one or more iterations based on activating one or more constraint points from the exterior constraint points and/or interior constraint points. The treatment planning process using the automatically generated envelope of constraint points may be repeated as often as desired until an acceptable treatment plan results, or until the planning process is terminated by the user.

In one embodiment, the treatment planning process may involve aspects of both forward and inverse planning techniques, thereby combining the strengths of forward and inverse planning techniques. For example, the operator can utilize isocentric beam geometries or a mixture of non-isocentric and isocentric beam geometries as part of forward planning and subsequently modify the topology of isodose contours directly during inverse planning using aspects of the optimization process described herein (e.g., the method described with respect to flowchart 800). The operator can control each beam for use in the treatment plan in terms of radiation emission point, a distance to the target region, an orientation, and a number of monitor units (MU). The treatment planning software can allow the operator to specify a set of beams (and associated paths, emission points, and dose weights) to be used as part of a forward planning process, and another set of beams to be used as part of inverse planning. The set of beams reserved for inverse planning may be optimized by utilizing one or more envelope of constraint points generated automatically by the treatment planning software.

Figure 10:
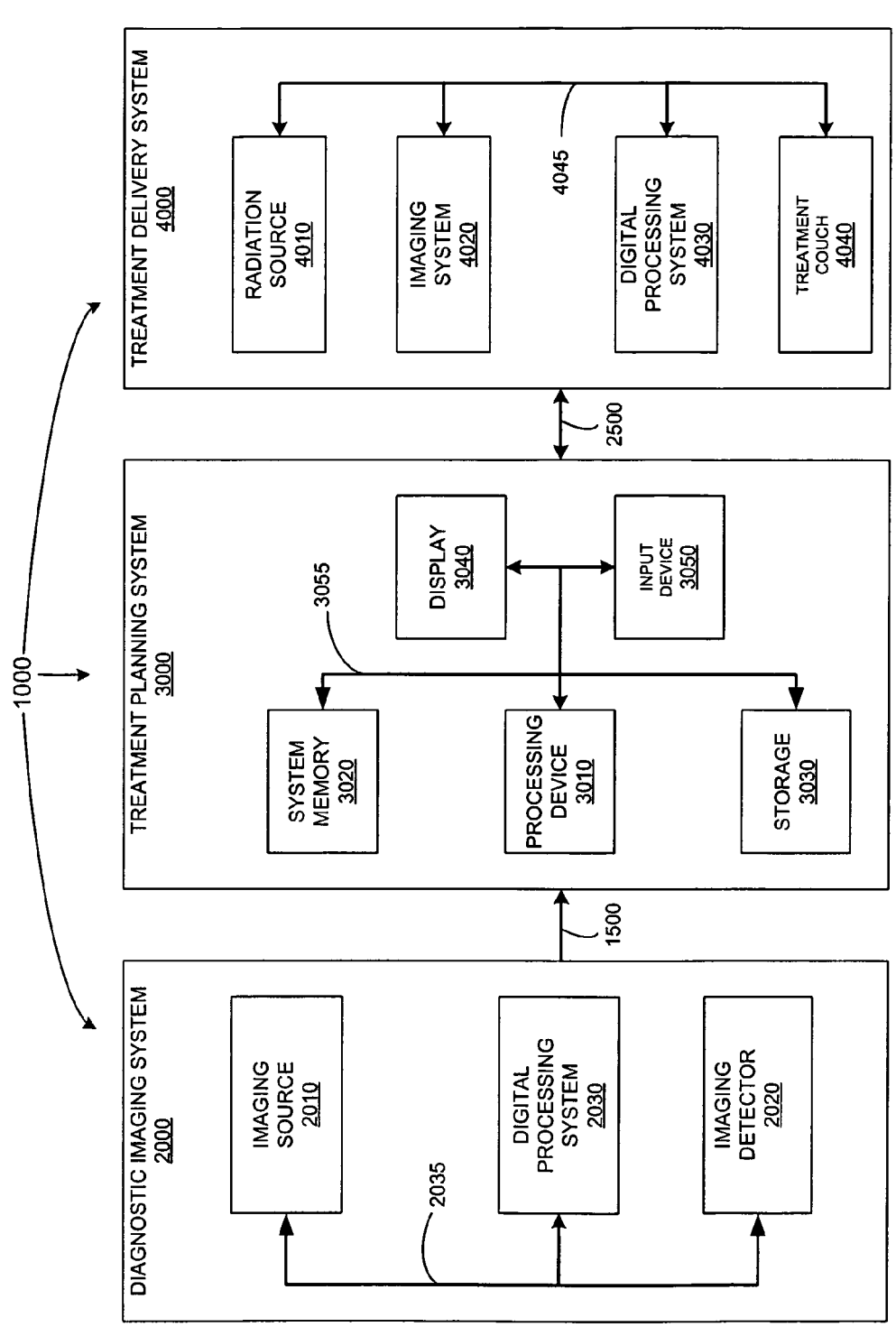
FIG. 10 illustrates one embodiment of systems that may be used to perform radiation treatment in which features of the present invention may be implemented.

FIG. 10 illustrates one embodiment of systems that may be used to perform radiation treatment in which features of the present invention may be implemented. As described below and illustrated in FIG. 10, system 1000 may include a diagnostic imaging system 2000, a treatment planning system 3000, and a treatment delivery system 4000.

Diagnostic imaging system 2000 may be any system capable of producing medical diagnostic images of a volume of interest (VOI) in a patient that may be used for subsequent medical diagnosis, treatment planning and/or treatment delivery. For example, diagnostic imaging system 2000 may be a computed tomography (CT) system, a magnetic resonance imaging (MRI) system, a positron emission tomography (PET) system, an ultrasound system or the like. For ease of discussion, diagnostic imaging system 2000 may be discussed below at times in relation to a CT x-ray imaging modality. However, other imaging modalities such as those above may also be used.

Diagnostic imaging system 2000 includes an imaging source 2010 to generate an imaging beam (e.g., x-rays, ultrasonic waves, radio frequency waves, etc.) and an imaging detector 2020 to detect and receive the beam generated by imaging source 2010, or a secondary beam or emission stimulated by the beam from the imaging source (e.g., in an MRI or PET scan). In one embodiment, diagnostic imaging system 2000 may include two or more diagnostic X-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s) which may be diametrically opposed to the x-ray sources. A single large imaging detector, or multiple imaging detectors, may also be used that would be illuminated by each x-ray imaging source. Alternatively, other numbers and configurations of imaging sources and imaging detectors may be used.

The imaging source 2010 and the imaging detector 2020 are coupled to a digital processing system 2030 to control the imaging operation and process image data. Diagnostic imaging system 2000 includes a bus or other means 2035 for transferring data and commands among digital processing system 2030, imaging source 2010 and imaging detector 2020. Digital processing system 2030 may include one or more general-purpose processors (e.g., a microprocessor), special purpose processor such as a digital signal processor (DSP) or other type of device such as a controller or field programmable gate array (FPGA). Digital processing system 2030 may also include other components (not shown) such as memory, storage devices, network adapters and the like. Digital processing system 2030 may be configured to generate digital diagnostic images in a standard format, such as the DICOM (Digital Imaging and Communications in Medicine) format, for example. In other embodiments, digital processing system 2030 may generate other standard or non-standard digital image formats. Digital processing system 2030 may transmit diagnostic image files (e.g., the aforementioned DICOM formatted files) to treatment planning system 3000 over a data link 1500, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 3000 includes a processing device 3010 to receive and process image data. Processing device 3010 may represent one or more general-purpose processors (e.g., a microprocessor), special purpose processor such as a digital signal processor (DSP) or other type of device such as a controller or field programmable gate array (FPGA). Processing device 3010 may be configured to execute instructions for performing treatment planning operations discussed herein, for example, automatically generating an envelope of constraint points based on the anatomical shape of a pathological anatomy, and optimizing a current dose isocontour utilizing the envelope of constraint points.

Treatment planning system 3000 may also include system memory 3020 that may include a random access memory (RAM), or other dynamic storage devices, coupled to processing device 3010 by bus 3055, for storing information and instructions to be executed by processing device 3010. System memory 3020 also may be used for storing temporary variables or other intermediate information during execution of instructions by processing device 3010. System memory 3020 may also include a read only memory (ROM) and/or other static storage device coupled to bus 3055 for storing static information and instructions for processing device 3010.

Treatment planning system 3000 may also include storage device 3030, representing one or more storage devices (e.g., a magnetic disk drive or optical disk drive) coupled to bus 3055 for storing information and instructions. Storage device 3030 may be used for storing instructions for performing the treatment planning steps discussed herein, such as the dilution and erosion algorithms.

Processing device 3010 may also be coupled to a display device 3040, such as a cathode ray tube (CRT) or liquid crystal display (LCD), for displaying information (e.g., a two-dimensional or three-dimensional representation of the VOI) to the user. An input device 3050, such as a keyboard, may be coupled to processing device 3010 for communicating information and/or command selections to processing device 3010. One or more other user input devices (e.g., a mouse, a trackball or cursor direction keys) may also be used to communicate directional information, to select commands for processing device 3010 and to control cursor movements on display 3040.

It will be appreciated that treatment planning system 3000 represents only one example of a treatment planning system, which may have many different configurations and architectures, which may include more components or fewer components than treatment planning system 3000 and which may be employed with the present invention. For example, some systems often have multiple buses, such as a peripheral bus, a dedicated cache bus, etc. The treatment planning system 3000 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 3000 may share its database (e.g., data stored in storage device 3030) with a treatment delivery system, such as treatment delivery system 4000, so that it may not be necessary to export from the treatment planning system prior to treatment delivery. Treatment planning system 3000 may be linked to treatment delivery system 4000 via a data link 2500, which may be a direct link, a LAN link or a WAN link as discussed above with respect to data link 1500. It should be noted that when data links 1500 and 2500 are implemented as LAN or WAN connections, any of diagnostic imaging system 2000, treatment planning system 3000 and/or treatment delivery system 4000 may be in decentralized locations such that the systems may be physically remote from each other. Alternatively, any of diagnostic imaging system 2000, treatment planning system 3000 and/or treatment delivery system 4000 may be integrated with each other in one or more systems.

Treatment delivery system 4000 includes a therapeutic and/or surgical radiation source 4010 to administer a prescribed radiation dose to a target volume in conformance with a treatment plan. Treatment delivery system 4000 may also include an imaging system 4020 to capture intra-treatment images of a patient volume (including the target volume) for registration or correlation with the diagnostic images described above in order to position the patient with respect to the radiation source. Treatment delivery system 4000 may also include a digital processing system 4030 to control radiation source 4010, imaging system 4020, and a patient support device such as a treatment couch 4040. Digital processing system 4030 may include one or more general-purpose processors (e.g., a microprocessor), special purpose processor such as a digital signal processor (DSP) or other type of device such as a controller or field programmable gate array (FPGA). Digital processing system 4030 may also include other components (not shown) such as memory, storage devices, network adapters and the like. Digital processing system 4030 may be coupled to radiation source 4010, imaging system 4020 and treatment couch 4040 by a bus 4045 or other type of control and communication interface.

Figure 11:
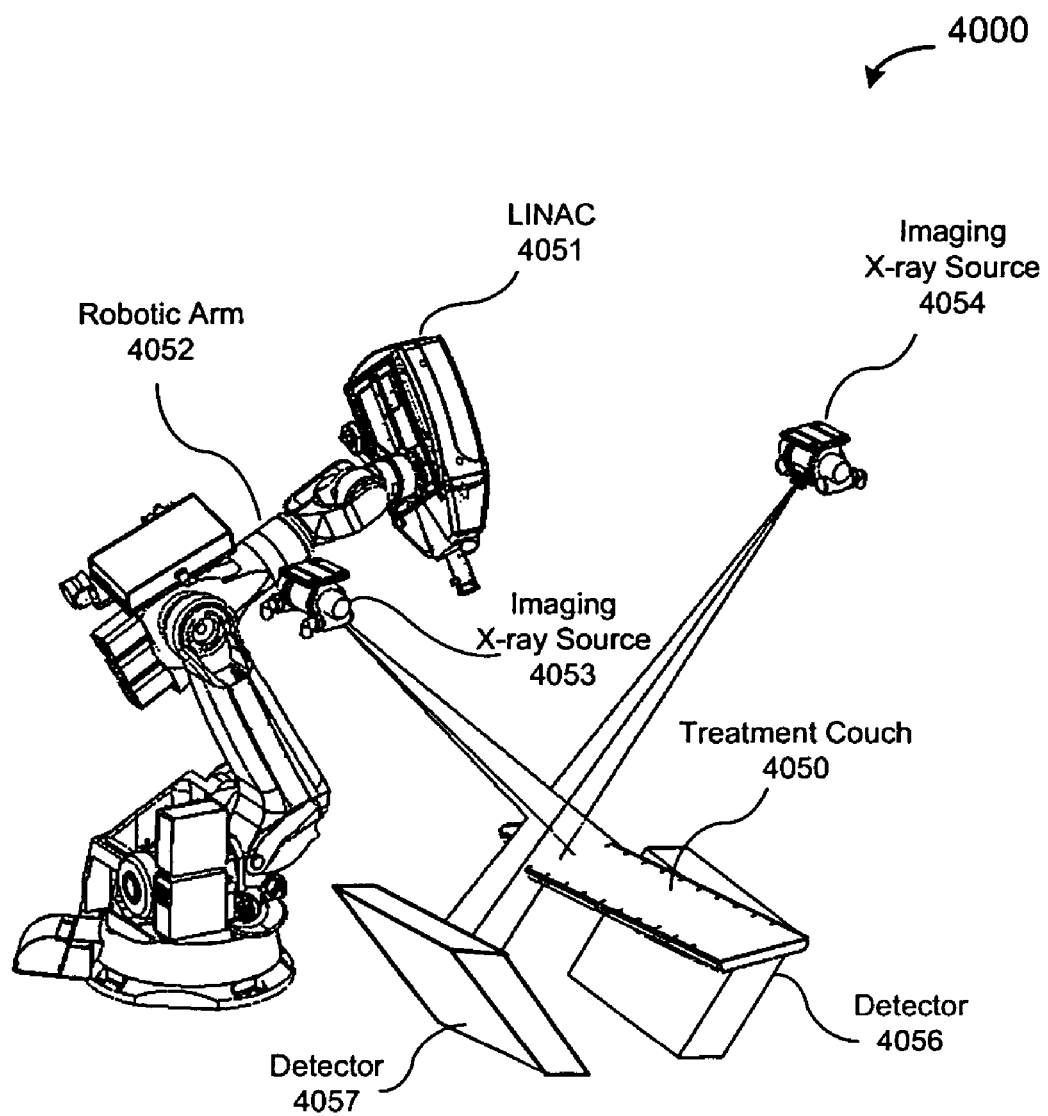
FIG. 11 illustrates one embodiment of a treatment delivery system.

In one embodiment, as illustrated in FIG. 11, treatment delivery system 4000 may be an image-guided, robotic-based radiation treatment system (e.g., for performing radiosurgery) such as the CyberKnife® system developed by Accuray Incorporated of California. In FIG. 11, radiation source 4010 may be represented by a linear accelerator (LINAC) 4051 mounted on the end of a robotic arm 4052 having multiple (e.g., 5 or more) degrees of freedom in order to position the LINAC 4051 to irradiate a pathological anatomy (target region or volume) with beams delivered from many angles in an operating volume (e.g., a sphere) around the patient. Treatment may involve beam paths with a single isocenter (point of convergence), multiple isocenters, or with a non-isocentric approach (i.e., the beams need only intersect with the pathological target volume and do not necessarily converge on a single point, or isocenter, within the target as illustrated in FIG. 9). Treatment can be delivered in either a single session (mono-fraction) or in a small number of sessions (hypo-fractionation) as determined during treatment planning. With treatment delivery system 4000, in one embodiment, radiation beams may be delivered according to the treatment plan without fixing the patient to a rigid, external frame to register the intra-operative position of the target volume with the position of the target volume during the pre-operative treatment planning phase.

In FIG. 11, imaging system 4020 may be represented by X-ray sources 4053 and 4054 and X-ray image detectors (imagers) 4056 and 4057. In one embodiment, for example, two x-ray sources 4053 and 4054 may be nominally aligned to project imaging x-ray beams through a patient from two different angular positions (e.g., separated by 90 degrees, 45 degrees, etc.) and aimed through the patient on treatment couch 4050 toward respective detectors 4056 and 4057. In another embodiment, a single large imager can be used that would be illuminated by each x-ray imaging source. Alternatively, other numbers and configurations of imaging sources and imagers may be used.

Digital processing system 4030 may implement algorithms to register images obtained from imaging system 4020 with preoperative treatment planning images in order to align the patient on the treatment couch 4050 within the treatment delivery system 4000, and to precisely position the radiation source with respect to the target volume.

The treatment couch 4050 may be coupled to another robotic arm (not illustrated) having multiple (e.g., 5 or more) degrees of freedom. The couch arm may have five rotational degrees of freedom and one substantially vertical, linear degree of freedom. Alternatively, the couch arm may have six rotational degrees of freedom and one substantially vertical, linear degree of freedom or at least four rotational degrees of freedom. The couch arm may be vertically mounted to a column or wall, or horizontally mounted to pedestal, floor, or ceiling. Alternatively, the treatment couch 4050 may be a component of another mechanical mechanism, such as the Axum® treatment couch developed by Accuray Incorporated of California, or be another type of conventional treatment table known to those of ordinary skill in the art.

Alternatively, treatment delivery system 4000 may be another type of treatment delivery system, for example, a gantry based (isocentric) intensity modulated radiotherapy (IMRT) system. In a gantry based system, a radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the isocenter to deliver a dose distribution to the target. In IMRT planning, the optimization algorithm selects subsets of the main beam and determines the amount of time that the patient should be exposed to each subset, so that the prescribed dose constraints are best met.

In other embodiments, yet another type of treatment delivery system 4000 may be used, for example, a stereotactic frame system such as the GammaKnife®, available from Elekta of Sweden. With such a system, the optimization algorithm (also referred to as a sphere packing algorithm) of the treatment plan determines the selection and dose weighting assigned to a group of beams forming isocenters in order to best meet provided dose constraints.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the application of radiation beam(s).

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method comprising:
   contouring a target region corresponding to a pathological anatomy; and
   automatically generating, using a processing device of a treatment planning system, an envelope of constraint points based on an anatomical shape of the pathological anatomy, wherein automatically generating further comprises forming an exterior surface with respect to the pathological anatomy with a dilation algorithm to position a set of exterior constraint points; and
   activating at least one constraint point from the envelope of constraint points to optimize a current radiation dose isocontour with respect to a target region contour for the target region.

2. The method of claim 1, wherein the envelope of constraint points have an initial dose weight of approximately zero.

3. The method of claim 1, wherein activating further comprises determining whether a constraint point from the set of exterior constraint points is inside of the current dose isocontour.

4. The method of claim 3, wherein activating further comprises:
   measuring a distance between the constraint point to the current dose isocontour; and
   assigning a weight value to the constraint point based on the distance.

5. The method of claim 1, wherein activating further comprises assigning an initial value of approximately zero to the envelope of constraint points.

6. The method of claim 1, wherein activating further comprises assigning a distance from the envelope of constraint points to a surface of the pathological anatomy.

7. The method of claim 1, wherein activating further comprises assigning a dose value to the envelope of constraint points relative to a prescribed dose for the pathological anatomy.

8. The method of claim 1, wherein automatically generating further comprises rolling a non-symmetric ellipsoid near a plurality of boundary points corresponding to the pathological anatomy.

9. The method of claim 8, wherein rolling further comprises:
calculating an ellipsoid mask volume for the pathological anatomy;
calculating a target volume of interest mask volume;
detecting a plurality of boundary points from the target volume of interest mask volume;
updating the target volume of interest mask volume for each boundary point of the plurality of boundary points; and
detecting a contour of a surface for the envelope of constraint points.

10. A method comprising:
contouring a target region corresponding to a pathological anatomy; and
automatically generating, using a processing device of a treatment planning system, an envelope of constraint points based on an anatomical shape of the pathological anatomy, wherein automatically generating further comprises forming an interior surface with respect to the pathological anatomy with an erosion algorithm to position a set of interior constraint points; and
activating at least one constraint point from the envelope of constraint points to optimize a current radiation dose isocontour with respect to a target region contour for the target region.

11. The method of claim 10, wherein activating further comprises determining whether a constraint point from the set of interior constraint points is outside of the current dose isocontour.

12. The method of claim 11, wherein activating further comprises:
measuring a distance between the constraint point to the current dose isocontour; and
assigning a weight value to the constraint point based on the distance.

13. An apparatus, comprising:
an imager to generate an image slice containing a target region corresponding to a pathological anatomy; and
a processing device coupled to the imager to receive the image slice, wherein the processing device is configured to contour a target region corresponding to the pathological anatomy and automatically generate an envelope of constraint points based on an anatomical shape of the pathological anatomy and form an exterior surface with respect to the pathological anatomy with a dilation algorithm to position a set of exterior constraint points, wherein the processing device is configured to activate at least one constraint point from the envelope of constraint points to optimize a current radiation dose isocontour with respect to a target region contour for the target region.

14. An apparatus, comprising:
an imager to generate an image slice containing a target region corresponding to a pathological anatomy; and
a processing device coupled to the imager to receive the image slice, wherein the processing device is configured to contour a target region corresponding to the pathological anatomy and automatically generate an envelope of constraint points based on an anatomical shape of the pathological anatomy form an interior surface with respect to the pathological anatomy with an erosion algorithm to position a set of interior constraint points, and wherein the processing device is configured to activate at least one constraint point from the envelope of constraint points to optimize a current radiation dose isocontour with respect to a target region contour for the target region.

15. A non-transitory machine readable medium having instructions thereon, which when executed by a processing device, cause the processing device to perform the following comprising:
contouring a target region corresponding to a pathological anatomy; and
automatically generating an envelope of constraint points based on an anatomical shape of the pathological anatomy, wherein automatically generating further comprises forming an exterior surface with respect to the pathological anatomy with a dilation algorithm to position a set of exterior constraint points; and
activating at least one constraint point from the envelope of constraint points to optimize a current radiation dose isocontour with respect to a target region contour for the target region.

16. The non-transitory machine readable medium of claim 15, wherein activating further comprises determining whether a constraint point from the set of exterior constraint points is inside of the current dose isocontour.

17. The non-transitory machine readable medium of claim 16, wherein activating further comprises:
measuring a distance between the constraint point to the current dose isocontour; and
assigning a weight value to the constraint point based on the distance.

18. The non-transitory machine readable medium of claim 15, wherein activating further comprises assigning an initial value of approximately zero to the envelope of constraint points.

19. The non-transitory machine readable medium of claim 15, wherein activating further comprises assigning a distance from the envelope of constraint points to a surface of the pathological anatomy.

20. The non-transitory machine readable medium of claim 15, wherein activating further comprises assigning a dose value to the envelope of constraint points relative to a prescribed dose for the pathological anatomy.

21. A non-transitory machine readable medium having instructions thereon, which when executed by a processing device, cause the processing device to perform the following comprising:
contouring a target region corresponding to a pathological anatomy; and
automatically generating an envelope of constraint points based on an anatomical shape of the pathological anatomy, wherein automatically generating further comprises forming an interior surface with respect to the pathological anatomy with an erosion algorithm to position a set of interior constraint points; and
activating at least one constraint point from the envelope of constraint points to optimize a current radiation dose isocontour with respect to a target region contour for the target region.

22. The non-transitory machine readable medium of claim 21, wherein activating further comprises determining whether a constraint point from the set of interior constraint points is outside of the current dose isocontour.

23. The non-transitory machine readable medium of claim 22, wherein activating further comprises:
measuring a distance between the constraint point to the current dose isocontour; and
assigning a weight value to the constraint point based on the distance.

* * * * *